United States Patent
Chou et al.

(10) Patent No.: US 6,858,742 B2
(45) Date of Patent: Feb. 22, 2005

(54) DNA LABELING REAGENTS, ACRIDINIUM-9-CARBOXAMIDE DERIVATIVES AND PROCESS OF PREPARING DNA LABELING COMPOUNDS

(75) Inventors: George Chin-Sheng Chou, Hsin-Shi (TW); Yu-Cheng Wu, Hsin-Shi (TW); Po-Ya Hsu, Hsin-Shi (TW)

(73) Assignee: AsiaGEN Corporation, Tainan Hsien (TW)

( * ) Notice: Subject to any disclaimer, the term of this patent is extended or adjusted under 35 U.S.C. 154(b) by 0 days.

(21) Appl. No.: 10/689,586

(22) Filed: Oct. 22, 2003

(65) Prior Publication Data
US 2004/0219564 A1 Nov. 4, 2004

Related U.S. Application Data

(62) Division of application No. 10/428,137, filed on May 2, 2003.

(51) Int. Cl.[7] .............................................. C07D 493/04
(52) U.S. Cl. ....................... 549/282; 546/104; 546/105; 546/303; 436/6
(58) Field of Search ........................... 549/282; 546/104

(56) References Cited

U.S. PATENT DOCUMENTS 4,312,883 A  *  1/1982  Baccichetti et al. ........ 514/455

* cited by examiner

*Primary Examiner*—Evelyn Mei Huang
(74) *Attorney, Agent, or Firm*—Troxell Law Office, PLLC

(57) ABSTRACT

The present invention relates to DNA labeling reagents comprising a furocoumarin derivative and a detectable group with or without bound via a binding enhancer, and acridinium-9-carboxamide derivatives for use as chemiluminescent labels. The present invention also relates to a process of preparing DNA labeling compound.

6 Claims, 3 Drawing Sheets

DNA LABELING REAGENTS, ACRIDINIUM-9-CARBOXAMIDE DERIVATIVES AND PROCESS OF PREPARING DNA LABELING COMPOUNDS

This application is a Divisional application of U.S. nonprovisional application Ser. No. 10/428,137, filed May 2, 2003.

FIELD OF THE INVENTION

The present invention relates to DNA labeling reagents and acridinium-9-carboxamide derivatives for use as chemiluminescent labels. The present invention also relates to a process of preparing DNA labeling compound.

BACKGROUND OF THE INVENTION

It's well known that, angelicin, an angular furocoumarin, could bind to double strand DNA through the UV radiated at 365 nm. The mechanism involved the [2+2] cycloaddition between (3,4) or (4,5)-double bonds of the furocoumarin and the 5,6 double bond of pyrimidine base on the double strand DNA. This photoreaction is directed to two steps reaction. The first step is furocoumarin and DNA formation of a molecular complex. The subsequent irradiation of the complex molecules at UV 365 nm leads to covalent binding of furocoumarins to DNAs. (L. Musajo et al., "Photoreactions at 3655A between pyrimidine bases and skin-photosensitizing furocoumarins, Photochemistry and Photobiology", Vol. 6, pp711–719, 6 (1967) and G. Rodighiero, et al, "Mechanism of skin-photosensitization by furocoumarins: photoreactivity of various furocoumarins with native DNA and with ribosomal RNA", Biochim. Biophys. Acta, 217, 40 (1970).

Several derivatives of the angelicin have been synthesized and compared their binding ability to DNA, including 4'-(hydroxymethyl)-4,5'-dimethylangelicin, 4'-(methoxymethyl)-4,5'-dimethylangelicin, and the hydrochloride of 4'-(aminomethyl)-4,5'-diemthylangelicin. The more water solubility of furocoumarin showed more binding ability to the DNA. (F. Dall'Acqua, et. al., "New monofunctional reagents for DNA as possible agents for the photochemotoerapy of psoriasis: Derivatives of 4,5'-dimethylangelcin", J. Med. Chem. 1981, 24,178–184).

Furocoumarins, which are linked to biotin with the suitable spacer molecules, have been shown to be very suitable for the photobiotinylation of nucleic acids. After hybridization to a gene probe with a complementary nucleic acid sequence, and a separation step, detection takes place, for example by addition of a complex of antibiotin antibody or avidin or streptavidin with alkaline phosphatase. For the detection, a color reaction, which is elicited by alkaline phosphatase, is carried out in an additional step (J. J. Leary, D. J. Brigati, D. C. Ward, Proc. Natl. Acad. Sci. USA 80, 4045–4049 (1983)).

In the description of U.S. Pat. No. 5,616,731, one disadvantage of the detection system using biotin is the wide distribution of biotin in biological systems. This disadvantage is avoided by using, for example, digoxigenin instead of biotin. Surprisingly, no denaturation of the nucleic acids has been observed in photoreactions with digoxigenin reagents, which are linked to furocoumarins by means of a suitable spacer.

Nicolaus Bahr et al., "A nitroxyl synthase catalytic antibody," J. Am. Chem. Soc. 1996, 118, 3550–3555 described the use of an antibody raised against acridinium hapten to analyze the retro Diels-Alder reaction of the anthracene-HNO cycloadduct to release anthracene and nitroxyl (HNO).

Maciej Adamczyk et al., "Neopentyl 3-Triflyloxypropanesulfonate" J. Am. Chem. Soc. 1998, 63, 5636–5639 described a reactive sulfopropylation reagent for the preparation of chemiluminescent labels.

SUMMARY OF THE INVENTION

The present invention relates to relate to DNA labeling reagents and acridinium 9-carboxamide derivatives for use as chemiluminescent labels.

The present invention also relates to a process of preparing DNA labeling compound.

DETAILED DESCRIPTION OF THE INVENTION

Figure 1:
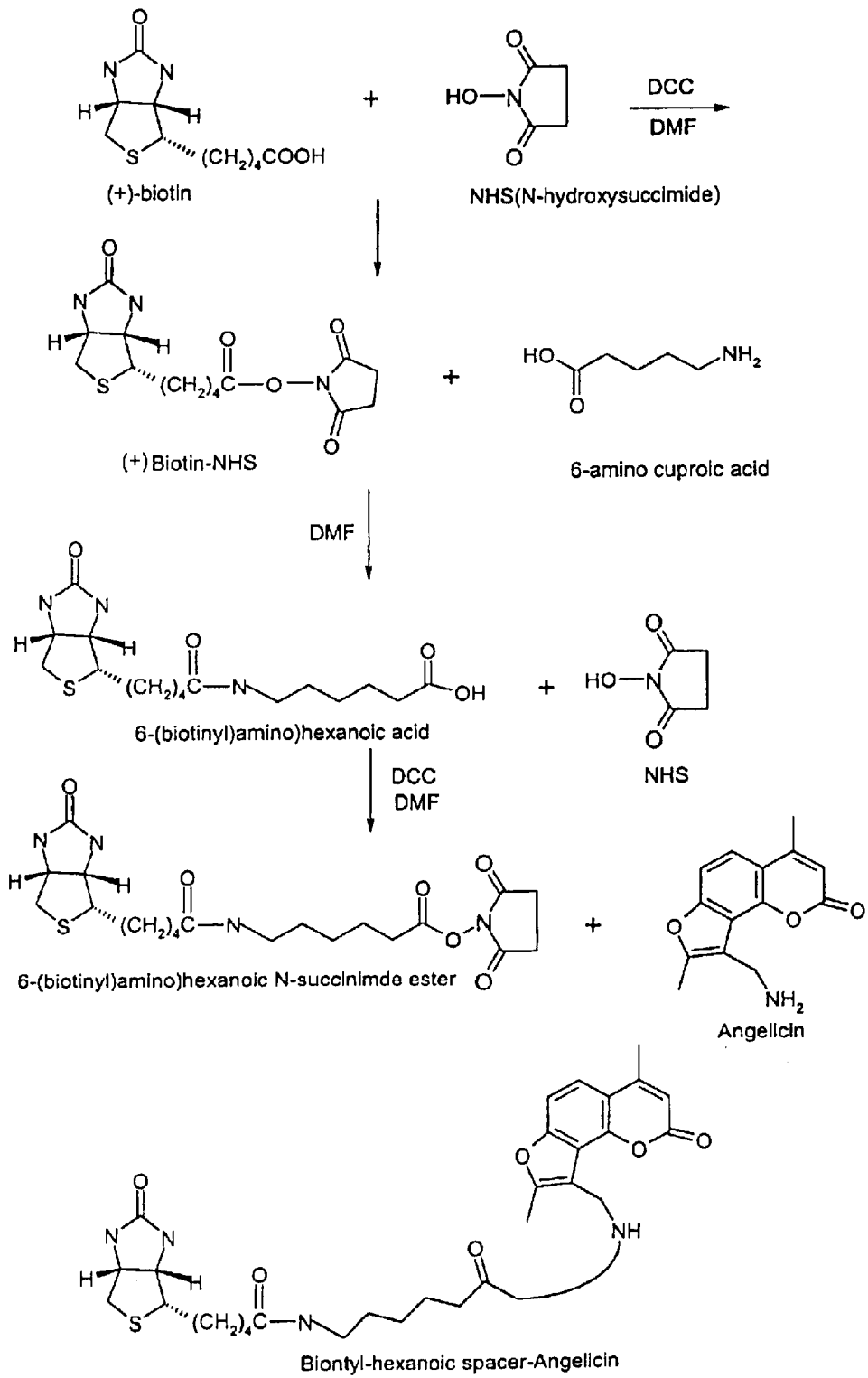
FIG. 1 illustrates synthesis of angelicin-binding enhancer-biotin.
Figure 2:
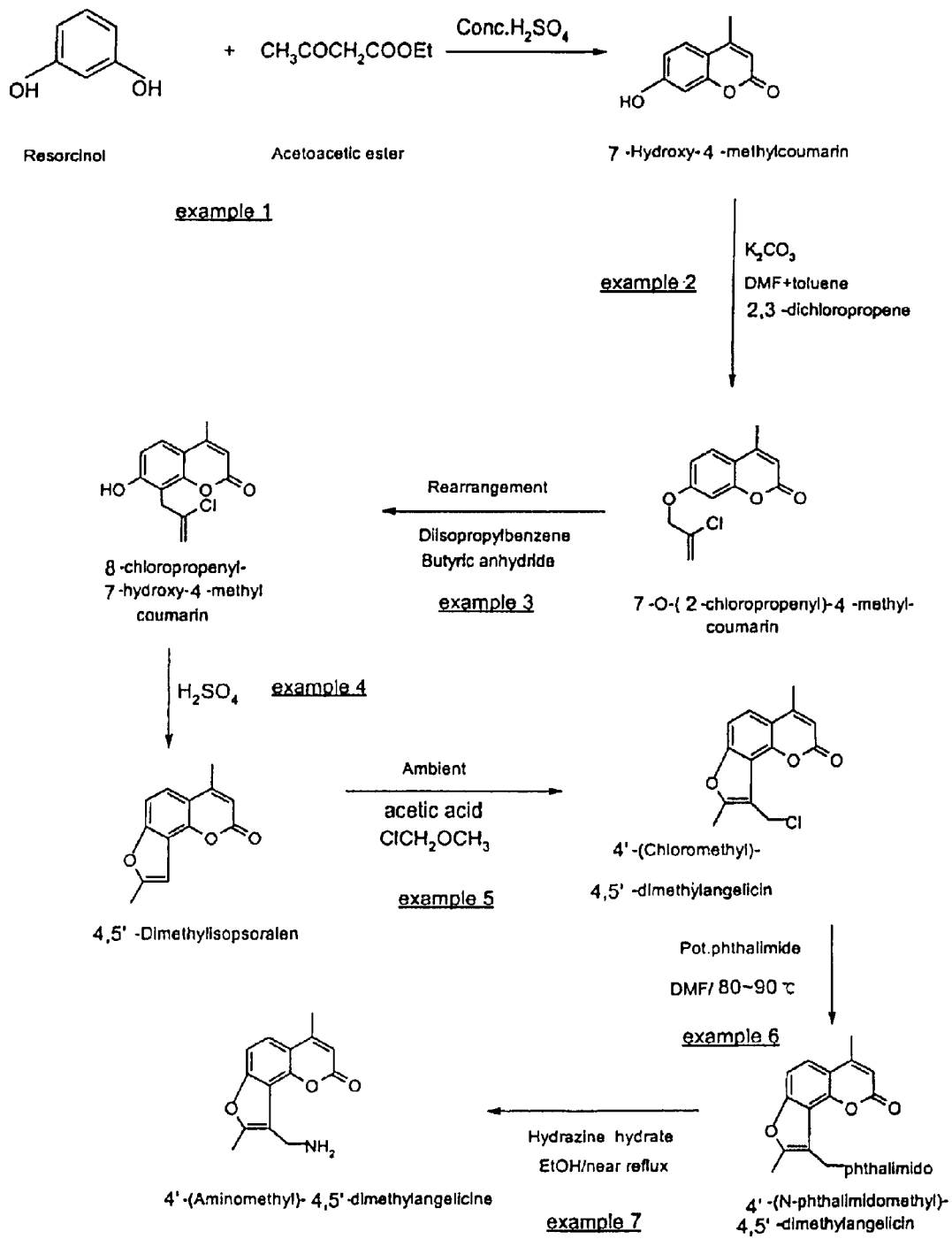
FIG. 2 illustrates synthesis of 4'-(aminomethyl)-4',5"-dimethylangelicin.
Figure 3:
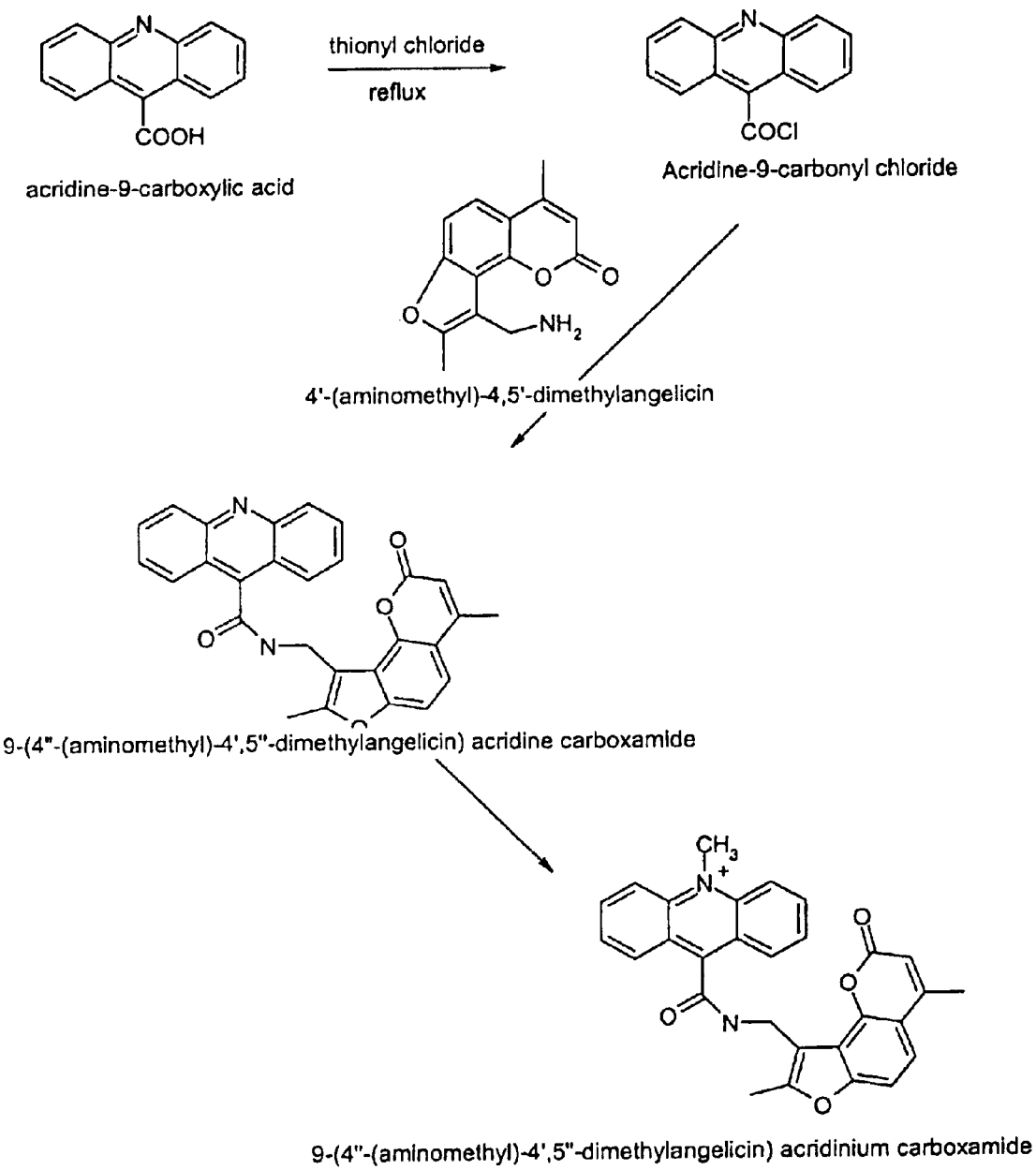
FIG. 3 illustrates synthesis of 9-(4"-(aminomethyl)-4',5"-dimethylangelicin)acridinium carboxamide.

The present invention relates to a DNA labeling reagent of the formula:

wherein Fu represents a furocoumarin derivative selected from the group consisting of angelicin derivatives and psoralen derivatives; wherein BE represents none or a binding enhancer selected from the group consisting of $C_{4-12}$ alkyl, alkyenyl, polyalkylamine and polyethylene glycol; and wherein D represents a detectable group selected from the group consisting of: biotin, fluorescence, acridinium ester and acridinium-9-carboxamide.

Furocoumarins

EP 187 332 mentions a number of literature references that describe the synthesis of furocoumarins and teaches elsewhere that other furocoumarins can be synthesized following published procedures. Therefore, the foregoing furocoumarins are either already known or they can be prepared in manner analogous to the known furocoumarins. For example, according to EP 187 332, Venema et al, Mol. Gen. Genet, describe angelicin. 179: 1 (1980); 4,5'-dimethylangelicin by Vedaldi et al, Chem. Biol. Interact., 36: 275 (1981); psoralen by Marciani et al, Naturforsch B, 27: 196 (1972); 8-methoxypsoralen by Belognzov et al, Mutat. Res., 84: 11 (1981), and by Scott et al, Photochem. Photobiol., 34: 63 (1981); 5-aminomethyl-8-methoxypsoralen by Hansen et al, Tet. Lett. , 22: 1847 (1981); 4,5,8-trimethylpsoralen by Ben-Hur et al, Biochem. Biophys. Acta, 331: 181 (1973); and 4'-aminomethyl-4,5,8-trimethylpsoralen by Issacs et al, Biochem., 16: 1058 (1977).

Other references disclose synthesis schemes suitable for preparing furocoumarins including Kaufman et al, J. Org. Chem., 45: 738 (1980); Wulff et al, J. Am. Chem. Soc., 110: 7419 (1988); U.S. Pat. No. 4,950,744, which issued Aug. 21, 1990, to Dattagupta et al; and U.S. Pat. No. 5,099,031, issued Mar. 24, 1992, to Mikhail et al.

In the DNA labeling reagent, the preferred embodiments of furocoumarins derivatives are angelicin derivatives. The further preferred embodiments of furocoumarins derivatives are acid salts of 4'-(Aminomethyl)-4,5'-dimethylangelicin.

Especially, the hydrochloride of 4'-(Aminomethyl)-4,5'-dimethylangelicin is excellent reagent to bind the DNA through the irradiation by UV 365 nm and showed good result in aqueous condition.

Binding Enhancers

The binding enhancer can avoid the stereo hindrance between binding group and DNAs and can increase the dark reaction during the first step to form the complex molecule between the furocourmarins and DNA. Suitable binding enhancers are described in EP 187 332. For instance, the binding enhancer could be $C_4$–$C_{12}$ alkyl, alkyenyl, polyalkylamine, polyethylene glycol or a combination thereof. However, without binding enhancer, the reagents comprising the furocoumarin derivatives and detectable group still could be used as DNA labeling reagent. In the DNA labeling reagent, the preferred embodiments of binding enhancers are $C_4$–$C_{12}$ alkyl or polyethylene glycol. $C_4$–$C_{12}$ alkyl is the most preferred embodiments.

Detectable Groups

The detectable groups could be biotin, fluorescence, Acridinium ester or acridinium-9-carboxamide.

In the DNA labeling reagent, the preferred embodiments of detectable groups are biotin, acridinium ester or acridinium-9-carboxamide.

Acridinium-9-carboxamide is the most preferred embodiments.

A process of preparing hydrochloride of 4'-(Aminomethyl)-4,5'-dimethylangelicin comprising the steps of (a) reacting 4'-(N-phthalimidemethyl)-4,5'-dimethylangelicin with hydrazine hydrate to produce a mixture;

(b) dissolving the mixture in organic extracting solvent;

(c) introducing acid gas into the organic layer of the mixture to form a precipitate; and (d) washing the precipitate with organic solvent.

In the step (a) of the process, the mixture is preferred under the condition of heating the mixture to solvent reflux. The solvent could be $C_{1-6}$ alkyl alcohol in which ethanol is the preferred embodiment. In the step (b) of the process, the organic extracting solvent in step (b) is halogenated alkanet in which chloroform is the preferred embodiment. It may use water to wash residues between step (b) and step (c). In step (c) of the process, acid gas was introduced into the organic layer of the mixture to form a precipitate. The acid gas could be any acid gas without affecting the formation of a precipitate. The most preferred embodiment is HCl gas. In the step (b) of the process, the organic solvent in step (d) is halogenated alkanet in Which chloroform is the preferred embodiment.

It is difficult to purify the hydrochloride of 4'-(aminomethyl)-4,5'-diemthylangelicin after synthesis. In conventional methods, after evaporated all the solvent, people extracted from chloroform and aqueous acid water, and this step lost a lot of the desired compound in water. If the solution extracted in base aqueous the desired compound hardly survived in that condition. After washed with water twice, the acid gas was purged into the chloroform and collected the precipitation, washed with chloroform to get the pure desired compound in high yield. This method can avoid the tedious procedure people used to operate and manufacture this compound in large scale. The following data prove the advantage of the present method over the extracted method.

| 20 g crude product | Recovery yield | Solvent consumed | Worked time |
|---|---|---|---|
| Extracted method | 30% | 4 L | 180 mins |
| HCl gas method | 90% | 0.5 L | 30 mins |

A compound of the formula:

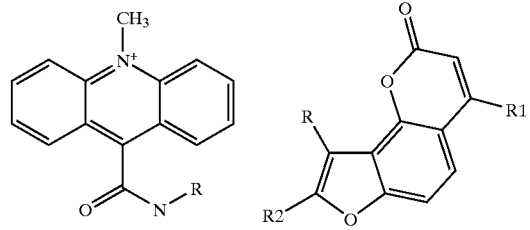

wherein R1 is H or $C_{1-6}$ alkyl or $C_{2-6}$ alkenyl; and R2 is H or $C_{1-6}$ alkyl or $C_{2-6}$ alkenyl.

The above compounds can be used as chemiluminescent labels. 9-(4"-(Aminomethyl)-4',5"-Dimethyl-angelicin) acridinium carboxamide is the preferred chemiluminescent label.

To prepare the acridinium-9-carboxamide from acridine-9-carboxylic acid, the mixture of acridine-9-carboxylic acid and thionyl chloride was heated to 80° C. for overnight. Removed all the thionyl chloride by reduced pressure and washed the yellow residue with hexane to afford the yellow crystal, acridine-9-chloride. Acridine-9-chloride could form acridine-9-carboxamide with any primary amine and secondary amine, and after methylation or ethylation to get the desired compound, acridinium-9-carboxamide derivatives.

Acridinium ester and acridinium-9-carboxamide would be hydrolysis in basic buffer and lost the chemiluminsence. As shown in Table 1, the chemiluminscene of acridinium ester is stronger than the acridinium-9-carboxamide. If these compounds were in basic buffer, the acridinium ester would be hydrolysis more than the acridinium-9-carboxamide.

TABLE 1

|  | Acridinium-9-carboxamide Derivatives | Acridinium ester Derivatives |
|---|---|---|
| Chemiluminescence in water (RLU/pmol) | $1–3 \times 10^7$ | $0.5–1 \times 10^8$ |
| Chemiluminescence in pH 8 Buffer at RT* 0 min (RLU/pmol) | $2 \times 10^7$ | $5 \times 10^7$ |
| Chemiluminescence in pH 8 Buffer at RT 5 mins (RLU/pmol) | $1.8 \times 10^7$ | $8 \times 10^6$ |
| Chemiluminescence in pH 8 Buffer at RT 10 mins (RLU/pmol) | $1.6 \times 10^7$ | $5 \times 10^5$ |
| Chemiluminescence in pH 8 Buffer at 60° C. 0 min (RLU/pmol) | $2 \times 10^7$ | $8 \times 10^6$ |
| Chemiluminescence in pH 8 Buffer at 60° C. 5 mins (RLU/pmol) | $8 \times 10^6$ | $3 \times 10^5$ |
| Chemiluminscence in pH 8 Buffer at 60° C. 10 mins (RLU/pmol) | $4 \times 10^6$ | $8 \times 10^4$ |

*RT is 25° C.

RLU is relative luminescence unit to measure the efficiency of chemiluminscene emitted. The machine we used to measure chemiluminsence is luminometer from Berthold. The buffer is 0.2M sodium tetraborate buffer.

EXAMPLES

The examples below are non-limiting and are merely representative of various aspects and features of the present invention.

Synthesis of Hydrochloride of 4'-(Aminomethyl)-4,5'-dimethylangelicin

Example 1

The Preparation of 7-hydroxy-4-methylcoumarin

Resorcinol (110 g, 1 mol) is mixed with ethylacetoacetate (130 g, 1 mol) and placed in a dropping funnel. This mixture is added drop wise to a chilled of sulfuric acid (150 mL) contained in the reactor with a mechanical stirrer and a thermometer. The rate of addition is such that the internal temperature did not exceed 20° C. After finished the drop wise, stirred 10 hours at room temperature. Poured this solution slowly into ice water with vigorous stirring.

Adjusted the pH to 6.5 with the aqueous sodium hydroxide. The product is collected by filtration, washed with water and air dry to afford 178 g (90%). mp. 165° C., $H^1$-NMR (300 Hz, $CD_3OD$): delta 7.58(d, 1H, J=8.8 Hz), 6.82(dd, 1H, J=8.8&2.4 Hz), 6.69(1H, d, J=2.4 Hz), 6.08(s, 1H), 2.49(s, 3H).

Example 2

The Preparation of 7-O-(2-chloropropenyl)-4-methylcoumarin 7-hydroxy-4-methyl coumarin (145 g, 0.82 mol) was mixed with 2,3-dichloro-1-propene (107 g, 0.95 mol) in 1 L dimethylforamide and 1 L toluene in the presence of potassium carbonate. The mixture is heated to toluene reflux for 18 hours. Filtrated the precipitation and the solvent was removed under reduced pressure and the residual extracted with chloroform (1 L) twice. The dry chloroform was filtered and the solvent removed under reduced pressure. Recrystallization from ethanol then collected the crystals and dried to afford 156 g (80%). m.p. 106° C. $H^1$-NMR (300 Hz $CD_3OD$): delta 7.57(d, 1H, J=9.0 Hz), 6.88(d, 1H, J=9.0 Hz), 6.11(s, 1H), 5.13(s, 1H), 4.95(s, 1H), 4.60(s, 1H), 3.83(s, 2H), 2.44(s, 3H).

Example 3

The Preparation of 8-chloropropenyl-7-hydroxy-4-methylcoumarin

A solution of 7-(2-chloro propenyl)-4-methyl coumarin (120 g, 0.48 mol) in a mixture of p-disopropyl-benzene (1 L) and n-butyric anhydride 160 mL was heated to 180° C. for 24 hours. The organic layer was evaporated under reduced pressure and residue recrystallizated from ethanol to afford 75 g of the desired compound.

Example 4

The Preparation of 4,5'-dimethylisopsoralen

A mixture of 8-chloropropenyl-7-hydroxy-4-methyl coumarin (48 g) and sulfuric acid (50 mL)was stirred at 0° C. overnight. The product was precipitated by methanol (300 mL) and cold water (2000 mL). The product is collected by filtration, washed with water till washing are neutral. The residue was recrystalized from methanol to afford the product 41 g (92%). $H^1$-NMR (300 Hz, $CDCl_3$): delta 7.42(d, 1H, J=8.8 Hz), 7.32(d, 1H, J=8.8 Hz), 6.72(s, 1H), 6.24(s, 1H), 2.50(s, 3H), 2.48(s, 3H).

Example 5

The Preparation of 4'-(chloromethyl)-4.5'-dimethylangelicin

A solution of 4,5'-dimethylisopsoraden (12 g) in acetic acid (100 mL) was added chloromethyl methyl ether (60 mL). The solution was stirred at room temperature for 56 hours. The solution was placed into the ice bath and the white precipitate collected by filtration to gave 11 g of the desired compound. $H^1$-NMR (300 Hz, $CDCl_3$): delta 7.42(d, 1H, J=8.8 Hz), 7.32(d, 1H, J=8.8 Hz), 6.24(s, 1H), 5.33(s, 2H), 2.50 (s, 3H), 2.48(s, 3H).

Example 6

The Preparation of 4'-(N-phthalimidemethyl)-4,5'-dimethylangelicin

The mixture of 4'-(chloromethyl)-4,5'-dimethyl angelicin (6.5 g) and potassium phthalimide (7.0 g) were dissolved in dimethylforamide (100 mL) and heated to 90° C. for 12 hours. Filtration out the solid, the solvent removed by reduced pressure. The desired compound (8.5 g) was collected from recrystallization. $H^1$-NMR (300 Hz, $CDCl_3$): delta 7.83(m, 2H), 7.68(m, 2H), 7.42(d, 1H, J=8.8 Hz), 7.30(d, 1H, J=8.8 Hz), 6.22(s, 1H), 5.19(s, 2H), 2.50(s, 3H), 2.48(s, 3H).

Example 7

The Preparation of Hydrochloride of 4'-(Aminomethyl)-4.5'-dimethylangelicin

The solution of 4'-(N-phthalimidemethyl)-4,5'-dimethylangelicin (20 g) in absolute ethanol (500 mL) was placed in the reactor, followed by addition hydrazine hydrate (7.5 mL) then heated the solution to ethanol reflux for 18 hours. The solvent was evaporated and the residues were dissolved in chloroform (300 mL) and washed water (300 mL) twice. While the volume of organic layer was reduced to half, the HCl gas was purged into the organic layer until the precipitation was emerged. The precipitation was collected and washed with chloroform (50 mL) to afford the desired compound (12 g). $H^1$-NMR (300 Hz, $CD_3OD$): delta 8.34(br, 2H), 7.67(d, 1H, J=8.8 Hz), 7.57(d, 1H, J=8.8 Hz), 6.39(s, 1H), 4.22(m, 2H), 2.50(s, 3H), 2.47(s, 3H).

Synthesis of Biotin-hexanoic Spacer-angelicin

Example 8

The Preparation of 6-(biotinyl)amino)hexanoic acid

The mixture of biotin (300 mg) and N-hydroxysuccimide (145 mg) were taken into reactor. After all the solid were dissolved in dimethylforamide (15 mL), added the dicyclohexanyl carbodiimide (0.2 mL) by syringe at 0° C. Stirred at room temperature for 36 hours. Filtered the precipitation and evaporated all the dimethylforamide, the residue washed with acetone to afford the desired compound, biotin-NHS. $H^1$-NMR (300 Hz, DMSO-d6): delta. 6.40(s, 1H), 6.35(s, 1H), 4.30(m, 1H), 4.14(m, 1H), 3.12(m, 1H), 2.80(m, 1H), 2.71(s, 4H), 2.65(m, 2H), 2.58(m, 2H), 1.72–1.43(m, 6H).

Biotin-NHS (1.4 g) and 6-amino cuproic acid (545 mg) were taken into the reactor, after dissolved in dimethylforamide (25 ml) completely, kept the reactor at room temperature for 24 hours. Filtered the solid and washed with acetone (15 ml) to afford the desired compound (950 mg). The yield is 75%, m.p.210° C., $H^1$-NMR (300 Hz, DMSO-d6): delta. 12.00(b, 1H), 7.72(t, 1H, J=5.4 Hz), 6.40(s, 1H), 6.34(s, 1H), 4.28(m, 1H), 4.11(m, 1H), 3.01(m, 1H), 2.98(m, 1H), 2.80(m, 1H), 2.54(m, 1H), 2.17(t, 2H, J=7.2 Hz), 2.02(t, 2H, J=7.2 Hz), 1.49–1.20(m, 12H).

Example 9

The Preparation of Biotin-hexanoic Spacer-angelicin 6-(biotinyl)amino)hexanoic acid (500 mg) and N-hydroxysuccimide (175 mg) were taken into the single neck reactor After all the solid were dissolved in 25 mL dimethylsulfide, added the dicyclohexanyl carbodiimide (0.47 mL) by syringe at 0° C. Stirred at room temperature for 36 hours. Filtered the solid and evaporated all the dimethylsulfide and washed the white solid with actone (10 mL) to afford the desired compound (180 mg). m.p. 182° C. $H^1$-NMR (300 Hz, DMSO-d6): delta. 12.00(br, 1H), 7.72(t, 1H, J=5.4 Hz), 6.40(s, 1H), 6.34(s, 1H), 4.28(m, 1H), 4.11(m, 1H), 3.01(m, 1H), 2.98(m, 1H), 2.80(m, 1H), 2.54 (m, 1H), 2.17(t, 2H, J=7.2 Hz), 2.02(t, 2H, J=7.2 Hz), 1.49–1.20(m, 12H).

BC-NHS (635 mg) and angelicin (290 mg) were taken into the single neck reactor. After all solid were dissolved in 25 mL dimethylsulfide, Stirred at room temperature for 36 hours. Filtered the precipitation and evaporated all the dimethylsulfide and washed the crystal with chloroform (10 mL). The desired product (400 mg) was obtained. m.p. 248° C. $H^1$-NMR (300 Hz, DMSO-d6): delta. 8.97(br, 1H), 7.67(br, 1H,), 7.61(d, 1H, J=8.8 Hz), 7.52(d, 1H, J=8.8 Hz), 6.39(s, 1H), 6.35(s, 1H), 6.33(s, 1H), 4.46(d, 2H, J=4.8 Hz), 4.28(m, 1H), 4.11(m, 1H), 3.01(m, 1H), 2.98(m, 2H), 2.80 (m, 1H), 2.54(m, 1H), 2.48(s, 3H), 2.45(s, 3H), 2.05(m, 4H), 1.49–1.17(m, 12H).

Synthesis of Acridinium Derivatives

Example 10

The Preparation of Acridinium-9-carboxamide Derivatives

A mixture of acridine-9-carboxylic acid (3 g) and thionyl chloride (20 mL) was heated to 80° C. for overnight. Removed all the thionyl chloride by reduced pressure and washed the yellow residue with hexane (15 mL) to afford the yellow crystal, acridine-9-chloride. The solution of acridine-9-chloride (0.37 mg) and 4'-(Aminomethyl)-4,5'-dimethylangelicin(0.37 mg) in chloroform (20 mL) was stirred at room temperature under argon for 30 mins. Evaporated all the solvent, the residue washed with methanol (10 mL) to afford the desired compound 9-(4"-(Aminomethyl)-4',5"-dimethylangelicin)acridine carboxamide. $H^1$-NMR (300 Hz, CDCl₃): delta 8.17(d, 2H, J=8.7 Hz), 7.84(d, 2H, J=8.7 Hz), 7.70(dd, 2H, J=8.7&7.2 Hz), 7.46(d, 1H, J=8.8 Hz), 7.40(d, 1H, J=8.8 Hz), 7.32(dd, 2H, J=8.7&7.2 Hz), 6.11(s, 1H), 5.02(d, 2H, J=7.5 Hz), 2.80(s, 3H), 2.47(s, 3H), 1.41(br, 1H).

The solution 9-(4"-(Aminomethyl)-4',5"-dimethylangelicin)acridine carboxamide (100 mg) and fluorosulfonic acid methyl ester (0.2 mL) in chloroform (15 mL) was stirred at room temperature for 30 hours. Filtration the precipitation and washed with ether (15 mL) to afford the desired compound, 9-(4"-(Aminomethyl)-4',5"-Dimethylangelicin)acridinium carboxam (54 mg). $H^1$-NMR (300 Hz, DMSO-d6): delta 9.70(br, 1H), 8.79(d, 2H, J=9.0 Hz), 8.52(d, 2H, J=8.4 Hz), 8.44(dd, 2H, J=8.4&7.5 Hz), 8.08(dd, 2H, J=9.0&7.5 Hz), 7.60(d, 1H, J=8.8 Hz), 7.56(d, 1H, J=8.8 Hz), 6.43(s, 1H), 5.02(d, 2H, J=7.2 Hz), 4.81(s, 3H), 2.65(s, 3H), 2.63(s, 3H).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. Thus, for example, in each instance herein any of the terms "comprising", "consisting essentially of" and "consisting of " may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. A process of preparing hydrochloride of 4'-(Aminomethyl)-4,5'-dimethylangelicin comprising the steps of
   (a) reacting 4'-(N-phthalimidemethyl)-4,5'-dimethylangelicin with hydrazine hydrate to produce a product compound;
   (b) dissolving the product compound in an organic extracting solvent to produce a mixture;
   (c) introducing HCL gas into an organic layer of the mixture to form a precipitate; and
   (d) washing the precipitate with organic solvent.

2. The process according to claim 1 wherein step (a) is under the condition of heating the mixture to a solvent reflux.

3. The process according to claim 2 wherein the solvent is ethanol.

4. The process according to claim 1 wherein the organic extracting solvent in step (b) is chloroform.

5. The process according to claim 1, which further comprises a washing step by the use of water between step (b) and step (c).

6. The process according to claim 1 wherein the organic solvent in step (d) is chloroform.

* * * * *